United States Patent [19]
DuBois

[11] 4,290,975
[45] Sep. 22, 1981

[54] N-SULFONYL AMINE-MEDIATED SULFAMATION OF AMINES

[76] Inventor: Grant E. DuBois, 4256 Ruthelma Ave., Palo Alto, Calif. 94306

[21] Appl. No.: 140,063

[22] Filed: Apr. 14, 1980

[51] Int. Cl.³ ........................................ C07C 143/86
[52] U.S. Cl. ............................ 260/513.6; 260/456 A; 549/33; 568/767
[58] Field of Search ..................... 260/456 A, 513.6

[56] References Cited
U.S. PATENT DOCUMENTS
4,097,521  6/1978  Merkle et al. .................... 260/513.6

Primary Examiner—Nicky Chan
Attorney, Agent, or Firm—William H. Benz

[57] ABSTRACT

Primary amines are selectively sulfamated by the two-step process of:
A. Contacting the amine in liquid phase at low to moderate temperatures with catechol sulfate thereby forming a catechol sulfate addition product, and
B. Hydrolyzing the catechol sulfate addition product to the desired sulfamate by contacting it at elevated temperature with a strong base in liquid phase.

10 Claims, No Drawings

N-SULFONYL AMINE-MEDIATED SULFAMATION OF AMINES

BACKGROUND OF THE INVENTION

1. Field of the Invention

This invention relates to a process for selectively sulfamating primary organic amines. More particularly, it relates to a two-step primary amine sulfamation process employing catechol sulfate.

2. The Prior Art

Over the years, many methods have evolved for sulfonation of primary amines. Interest in the cyclamate class of nonnutritive sweeteners and in heparin and analogs as anticoagulants has been largely responsible for the development of synthetic methods of sulfamic acid salt preparation. Methods in current use include (1) sulfonation of amines with chlorosulfonic acid: see (Gilbert, E. E., "Sulfonation and Related Reactions"; Interscience: New York, 1965; Chapter 7 and references therein); (see Bieber, T., Amer. Chem. Soc., 1953, 75, 1405); (see Bieber, T., J. Amer. Chem. Soc., 1953, 75, 1409); (See Weiss, G., Schulze, G., Ann., 1969, 729, 40). While these methods have utility with simple amine group- or amine-precursor-containing materials, they present the problem of being nonselective when other functionalities such as hydroxyls and the like are present and thus lead to poor yields of desired sulfonate products.

For example, while studying the dihydrochalcone class of nonnutritive sweeteners, we wished to prepare intensely sweet sulfamoethyl dihydrochalcone 1.

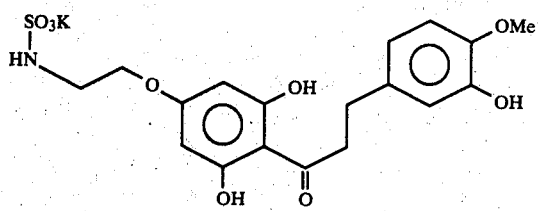

Synthesis of 1 via sulfonation of the corresponding amine with $Me_3N.SO_3$, the mildest of the commonly employed N-sulfonating agents, was plagued by an inability to achieve selective N-sulfonation and problems in removal of the foul-smelling $Me_3N$ after conversion of the intermediate trimethylammonium salt to the potassium salt. The product thus obtained required preparative HPLC purification and was obtained in only 15-20% yield.

Clearly, a selective method of amine sulfamation is needed which is compatible with labile functionality such as is present in 1.

Compound 1 and its precursors are the subject of United States Patent application Ser. No. 140,064, filed of even date herewith and incorporated by reference herein.

STATEMENT OF THE INVENTION

It has been found that primary organic amines can be selectively sulfamated, even when other labile functionalities are present, by the following two-step process:

First, the amine is contacted in liquid phase with catechol sulfate. The amount of catechol sulfate is selected to provide at least one mole of catechol sulfate per mole of amine to be sulfamated and not more than about one-half mole per mole of total amine present. This contacting is carried out at low to moderate temperatures such as from about $-30°$ C. to about $50°$ C. The product of this step is an O-2-hydroxyphenol sulfamic acid ester.

In the second step, this ester is hydrolyzed to the desired sulfamate by reaction with a strong base at moderate to elevated temperatures.

DETAILED DESCRIPTION OF THE INVENTION

The present process employs catechol sulfate to effect sulfamation of organic amines.

Catechol Sulfate. This material is a known compound having the structural formula

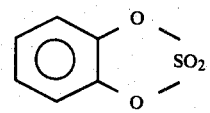

Its preparation is disclosed at Denivelle, L., Compt. Rend., 203, 1936, 194., as well as herein in the Examples.

The Amines. The amines sulfamated by this invention are primary organic amines. It has been found that secondary amines will react with the catechol sulfate in good fashion, but that the addition product does not facilely hydrolyze to give the ultimately desired sulfamate salt product. The primary amines treated by the present process can range from simple molecules such as simple primary alkyl or aryl amines, for example, propylamine, cyclohexylamine, hexadecylamine, aniline, benzylamine or the like, to more complex materials such as amine-containing drugs, dyes, biologically active materials and the like, and can include primary alkyl and aromatic amines of from 2 to about 40 carbon atoms. While it is not intended to limit the scope of this invention to any particular group or class of amine-containing compounds, it is generally considered to be most advantageous to employ the present process to sulfamate amines which contain in their structure other labile groups which would be expected to undergo side reactions with art-taught sulfamation processes. Such labile groups include aldehyde and ketone carbonyls, alkanol and phenol hydroxyls, carboxylic acid and ester groups and the like.

THE PROCESS CONDITION

This process has two steps—a catechol sulfate addition step and a hydrolysis step.

The catechol sulfate addition step may be carried out as follows: Catechol sulfate and the amine are admixed in liquid phase at low to moderate temperature. As reaction medium is employed a liquid which dissolves the catechol sulfate and the amine. Methylene chloride, chloroform, carbon tetrachloride, ethylene chloride and other halocarbons are suitable reaction media and are generally preferred. Other suitable media include ethers and ketones. Generally, a polar solvent is preferred with a polar halocarbon, especially methylene chloride, being most preferred.

The first reaction step is generally carried out as a batch process, with stirring. The reaction temperature for the first step is generally a low to moderate temperature. In general, the lower the temperature, the more selective the reaction with the amine groups. The optimum temperatures employed depend upon the amine being sulfamated as aromatic amines tend to be less reactive and require higher temperatures than the more reactive alkyl amines. Temperatures in the range of −30° C. to 50° C. can be used with the higher portion of the range (0° to 50° C.) favoring the aromatic amines—the lower portion (−30° to +15° C.) favoring the alkyl amines. With alkyl amines, a preferred range of temperature is −5° to +5° C.; with aromatic amines, 15° to 50° is a preferred range. Reaction times required range from about 1 hour to as much as 72 hours and are inversely proportional to the reaction temperature. At the preferred temperatures, times of 1 to 20 hours are preferred.

The relative amounts of amine and catechol sulfate are generally controlled. Ideally, about 2 moles of total amine are used per mole of catechol sulfate. The mechanism for the reaction shows that two equivalents of amine are needed, one to effect opening of the catechol sulfate and the second to deprotonate the amine cation.

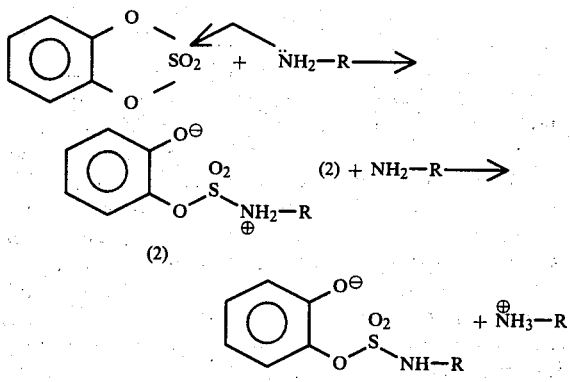

Excess weak base amines favor this reaction, but excess strong base does not. If gross excesses of strong base are present, two hydrogens can be abstracted from the amine group giving rise to the dianion

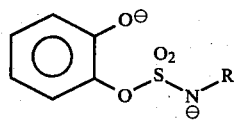

a species which is relatively nonreactive.

When sulfamating an inexpensive amine, such as cyclohexylamine or the like, it is convenient to simply use an excess of this amine such as from say 1.5 to 5, preferably 1.8 to 3 and most preferably about 2 equivalents of amine basis catechol sulfate. However, if the primary amine to be sulfamated is a costly material, employing such excesses would be uneconomic. In these cases it is more reasonable to replace a portion of the primary amine with an inexpensive tertiary amine such as a lower alkyl tertiary amine, for example, trimethylamine, triethylamine or the like, still maintaining the above-noted total amine: catechol sulfate ratios. If a tertiary amine is present, the ratio of primary amine:catechol sulfate is held at about 1:1, that is, from say about 1.2:1 to about 1:1.2 with the amount of tertiary amine being such as to raise the total amine catechol sulfate molar ratio to the above-noted ranges.

The reaction product of this first step can be used directly in the second step, if desired. It should be noted, however, that if an excess of catechol sulfate was used in the first step and thus is present in this mixture, the higher temperature of the second step could lead to undesired sulfonation side reactions. If, as is preferred, the catechol sulfate addition product of the first reaction is isolated before effecting the second reaction, this may be carried out by such art-known techniques as evaporation of solvent, titration with aqueous mineral acid and extraction with an organic solvent or the like. Thereafter, the isolated product may be purified further by extraction, crystallization, column chromatography, TLC and the like. On a laboratory scale, recrystallization has been used successfully to recover the catechol sulfate addition products and for reasons of convenience is generally the recovery method of choice.

The second step, the hydrolysis, is conducted by contacting the catechol sulfate addition product with a strong inorganic base in liquid phase. The amount of base is at least one equivalent, based on the catechol sulfate addition product, with extra base being needed if the particular amine addition product contains any groups which would consume base. For example, if the amine being sulfamated contains two acidic protons, it will be desirable to add two additional equivalents of base to neutralize them. It is preferred to use from 1.0 to 1.5 equivalents of strong base based on the catechol sulfate addition product plus any additional base, as set forth above. Alkali metal or alkaline earth metal hydroxides, especially NaOH, KOH, Ca(OH)$_2$ and Mg(OH)$_2$ are preferred bases with NaOH and KOH being most preferred.

Water is an excellent reaction medium for this step and is preferred. If desired, other nonreactive base-dissolving liquids may be employed as may their mixtures with water.

The hydrolysis step is carried out at elevated temperatures. Atmospheric reflux temperatures of 95°–105° C. are very convenient and suitable. Generally, temperatures of about 50° C. to about 200° C. may be used, so long as the amine is stable. Preferred temperatures range from 50° to 120° C. At the higher temperatures, superatmospheric pressures may be employed.

This step is relatively quick, at low temperatures requiring up to about 12 hours. At the highest temperatures, the reaction goes to completion in as little as a minute. At the preferred temperatures, times of from 0.5 to 4 hours are suitably employed.

Following this second step, the reaction mixture may be worked up and the sulfamated product recovered. This work up will generally include neutralization of excess base, and reprotonation of the acidic hydrogens in the amine by acid addition such as to pH 5–7. The final isolation of the sulfamate product can employ conventional techniques such as extraction, precipitation and chromatography. Simple recrystallization is quite effective.

The invention will be further described by the following Examples and Preparations. These are provided solely to illustrate the present invention. They are not to be construed as limiting its scope.

EXAMPLES AND PREPARATIONS

In the Examples and Preparations all temperatures are expressed in degrees centigrade. Where infrared spectra are noted, they were recorded on a Perkin Elmer Model 137 spectrophotometer. Proton magnetic resonance spectra were recorded on a Varian Associates T-60A spectrometer (60 MHz) and are recorded in parts per million from tetramethylsilane on the δ scale. Data are reported as follows: chemical shift, multiplicity (s=singlet, d=doublet, t=triplet, q=quartet, m=multiplet, br=broad), coupling constant (Hz), integration, and interpretation. Ultraviolet spectra were recorded on a Varian Associates Cary 118 Spectrophotometer. Melting points were determined on a Fisher-Johns melting point apparatus.

High-pressure liquid chromatography (HPLC) was performed on a Waters Associates system equipped with a Model 660 Solvent Programmer, two Model M-6000A pumps and a Schoeffel Instrument Corporation variable wavelength ultraviolet detector and a 30 cm C-18 on μ-Bondapak column. Vapor phase chromatography (VPC) was carried out on a Varian Associates Aerograph Model 920 employing a six foot 5% SE-30 on chromosorb G column. Thin layer chromatography (TLC) was carried out on EM Laboratories pre-coated silica gel 60 F-254 plates (b×10 cm).

Diethyl ether, hexane, ethylacetate, chloroform and methylene chloride used were reagent grade solvents from J. T. Baker Chemical Co. Triethylamine was distilled from phosphorus pentoxide and stored over activated molecular sieves 4A. Dimethylformamide (DMF) was distilled from calcium hydride and stored over activated molecular sieves 4A. Pyridine was distilled from barium oxide and stored over activated molecular sieves 4A. Sulfuryl chloride was subjected to simple distillation prior to use.

PREPARATION OF CATECHOL SULFATE

Fifty-five g (0.50 mol) of catechol was dissolved in 79 g of pyridine while stirring vigorously with an overhead stirrer under dry argon in a one-liter, three-necked flask equipped with a thermometer and addition funnel. Five hundred ml hexane was then added after which the reaction mixture was cooled to −5° in an ice-salt bath. A solution of 68 g (0.50 mol) of sulfuryl chloride in 100 ml hexane was then added dropwise over 4 hours while carefully maintaining the temperature between −5° and 0°. Stirring at 0° C. was continued overnight after which the reaction mixture was allowed to warm to ambient temperature over 6 hours. The upper layer of the two-layer reaction mixture was decanted after which the lower layer was washed (2×100 ml) with ethyl acetate. The combined washes and upper layer were then washed with 5% Cu(OAc)$_2$.H$_2$O until TLC (hexane-ethylacetate; 3:1) indicated the absence of catechol ($R_f$=0.14). The solution was then dried over magnesium sulfate and concentrated yielding 56.7 g of an amber liquid. TLC (hexane-ethylacetate; 3:1) showed one component having $R_f$=0.40. VPC (165° C.; 60 cc/min He flow) showed one major component having RT=5.0 min contaminated by an impurity at 7.5 min. Distillation through a 15 cm vigreux column yielded 45.1 g (52%) of a colorless liquid having bp 76°–8° C. (1.25 mm). Recrystallization from hexane yielded 38.0 g of long, colorless needles having mp 35.5°–36° C. (lit mp 34°–5°).

EXAMPLE I

Sulfonation of Benzylamine

Step A. Addition of Catechol Sulfate

Forty-four mmol (4.71 g) of benzylamine was added dropwise via syringe over 2–3 minutes to a solution of 3.55 g (20.0 mmol) of catechol sulfate in 50 ml methylene chloride while stirring under dry argon at 0° C. After slowly warming to ambient temperature over 12 hours, the reaction mixture was poured into 100 ml of 2% hydrochloric acid and extracted with ether (3×50 ml), and the combined portions were washed with 2% HCl (4×25 ml), water (2×25 ml), dried over magnesium sulfate and concentrated, yielding 5.70 g of a white solid. Recrystallization from hexane-chloroform yielded 5.48 g (98%) of colorless, long needles of N-benzyl-O-(2-hydroxy-phenyl)-sulfamate having mp 116.5°–117.5° C. TLC (chloroform-methanol; 95:5) showed one component having $R_f$=0.37. IR (KBr) 2.97 (O—H), 3.07 (N—H), 3.45, 3.52, 6.29, 6.63, 6.87, 6.99, 7.43, 7.75, 8.23, 8.45, 8.65, 9.15, 9.42, 10.71, 11.13, 11.43, 12.37, 13.25, 13.40μ; NMR (CDCl$_3$) δ 4.42 (s, 2H, PhCH$_2$), 5.00 (br, 1H, NH), 6.83–7.33 (m, 10H, aromatic H and O—H); UV (EtOH) λ$_{max}$ (ε) 274 nm (ε=2390) Anal. Calcd. for C$_{13}$H$_{13}$NO$_4$S:C, 55.90; H, 4.69. Found: C, 55.73; H, 4.66.

Step B. Hydrolysis of Catechol Sulfate Addition Product

Twenty mmol of 1.00 M potassium hydroxide were added to 2.79 g (10.0 mmol) of N-benzyl-O-(2-hydroxyphenyl)sulfamate in a 100 ml one-necked flask equipped with a magnetic stir bar. Forty ml distilled water was then added and the reaction apparatus was purged with argon. The reaction mixture was then refluxed vigorously for 30 minutes when TLC of an aliquot indicated the absence of starting material. The pH was adjusted to 5–6 by addition of 2% hydrochloric acid and the reaction mixture concentrated to dryness at reduced pressure. The white solid thus obtained was then extracted with boiling ether (3×25 ml) and dried in vacuo, to give 2.22 g (99% yield) of the acid salt. HPLC (10% methanol in 0.03 M NaH$_2$PO$_4$; 254 nm) showed only one peak having RT=5.4 min. Recrystallization from distilled water yielded an analytical sample that did not melt, but seemed to soften at ~ 205° C. IR (KBr) 3.08 (N—H), 3.29, 3.47, 6.90, 8.03, 8.24, 8.50, 9.56, 12.85, 13.83, 14.50μ; NMR (DMSO d$_6$) δ 3.95 (d, J=7 Hz, 2H, PhCH$_2$), 4.66 (t, J=7 Hz, 1H, N—H), 7.27 (m, 5H, aromatic H); UV (H$_2$O) λ$_{max}$ (ε) 252 nm (ε=164), 257 nm (ε=201), 263 nm (ε=156).

EXAMPLE II

Sulfamation of Cyclohexylamine

Step A. Addition of Catechol Sulfate

Forty-four mmol (4.36 g) of cyclohexylamine was reacted with 20 mmol catechol sulfate as in Part A. of Example I above. Recrystallization of the crude product from hexane-chloroform yielded 5.00 g (92%) of tiny needles of N-cyclohexyl-O-(2-hydroxyphenyl) sulfamate having mp 71°–3° C. TLC chloroform-methanol; 95:5) showed one component having $R_f$=0.38. IR (KBr) 2.97 (O—H), 3.03 (N—H), 3.40, 3.49, 6.65, 6.94, 7.50, 8.22, 8.47, 9.30, 10.70, 11.50, 12.61, 13.23, 14.13μ; NMR (CDCl$_3$) 0.15–2.30 (m, br, 10H, (CH$_2$)$_5$), 3.40 (m, br, 1H, C—H), 5.67 (br, 2H, N—H, O—H), 6.70–7.43 (m, 4H, aromatic H); UV (ETOH) λ$_{max}$ (ε) 274 nm (ε=2510).

Step B. Hydrolysis of Catechol Sulfate Addition Product

Treatment of 543 mg (2.00 mmol) of N-cyclohexyl-O-(2-hydroxyphenyl)-sulfamate according to the general hydrolytic procedure shown in Example I, Part B. yielded 431 mg (99%) of N-Cyclohexyl sulfamic acid, potassium salt. Recrystallization from distilled water yielded large platelets as an analytical sample. IR (KBr) 3.10 (N—H), 3.41, 3.50, 6.94, 7.73, 8.06, 8.40, 9.65, 10.91, 11.21, 11.40, 12.47, 13.82μ; NMR (D₂O) 0.80–2.50 (m, BR, 10H, (CH₂)₅), 3.06 (m, Br, 1H, CH).

EXAMPLE III

Alternate to Example I, Part A

A solution of 1.89 g (11.0 mmol) catechol sulfate in 2.0 ml methylene chloride was added dropwise while stirring vigorously at 0° C. under dry argon to a solution of 1.07 g (10.0 mmol) benzylamine and 1.11 g (11.0 mmol) of triethylamine in 25 ml of DMF. After 2.5 hours at 0° C., the reaction mixture was poured into 100 ml 1% hydrochloric acid and extracted with ether (3×25 ml), the combined portions were washed with water (6×50 ml), dried over magnesium sulfate and concentrated yielding 2.93 g of a white solid. Recrystallization from chloroform yielded 2.48 g (89%) of long needles of the product of Example I, Part A.

EXAMPLE IV

Sulfamation of an Aminodihydrochalcone Containing Other Labile Functionalities

A. Addition of Catechol Sulfate

Using the general method of Example III, 991 mg (2.85 mmol) of 2,3',6-trihydroxy-4'-methoxy-4-aminoethoxy dihydrochalcone was reacted with 541 mg (3.14 mmol) of catechol sulfate in 15 ml DMF in the presence of 318 mg (3.14 mmol) triethylamine. Recrystallization of the crude product from chloroform yielded 1.14 g (77%) of light tan, granular crystals of N-(2,3',6-trihydroxy-4'-methoxydihydrochalcone-4-ethoxy)-O-(2-hydroxyphenyl) sulfamate[1] having mp 78°–80° C. TLC (chloroform-methanol; 95:5) showed one component having $R_f=0.11$. IR (KBr) 2.93 (O—H, N—H), 3.42, 3.50, 6.17 (C=O), 6.33, 6.63, 6.70, 7.01, 7.38, 8.00, 8.35, 8.54, 8.65, 9.25, 9.74, 10.41, 11.37, 12.23, 12.42, 13.16, 14.22μ; NMR (acetone d₆) 2.86 (t, J=7 Hz, 2H, Ar—CH₂), 3.36 (t, J=7 Hz, 2H, Ar COCH₂), 3.63 (t, J=6 Hz, 2H, N=CH₂), 3.82 (s, 3H, O—CH₃), 4.14 (t, J=6 Hz, 2H, N—C—CH₂—O), 5.97 (s, 2H, ArCO aromatic H), 6.64–7.50 (m, 7H, aromatic H); UV (EtOH) $\lambda_{max}$ 283 nm ($\epsilon=21,900$).

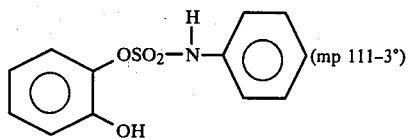

B. Hydrolysis

Treatment of 5.20 g (10.0 mmol) of 1.0 with 20.0 mmol potassium hydroxide according to the general procedure of Example I., Step B, for 60 minutes yielded 4.66 g of a light tan solid. HPLC (10–100% MeOH in 0.03 M KH₂PO₄ linear gradient; 15 min program; 2.0 ml/min; 286 nm) showed the desired product (RT-12.0 min) contaminated by 7% of an unknown impurity (RT-13.5 min). Comparison with a standard solution of authentic material indicated a yield of 4.23 g (91%) of N-(2,3',6-trihydroxy-4'-methoxy-dihydrochalcone-4-ethoxy)-sulfamic acid, potassium salt (2.0). Recrystallization from distilled water yielded 2.79 g (60%) of tiny white, granular crystals. IR (KBr) 2.95 (O—H), 3.03 (N—H), 3.40, 3.52, 6.17 (C=O), 6.27, 6.60, 7.00, 7.71, 8.10, 8.53, 8.89, 9.21, 9.63, 10.61, 12.13, 12.40, 13.17; NMR (DMSO d₆) 2.97 (t, J=6 Hz, 2H, Ar—CH₂), 3.16 (t, J=6 Hz, 2H, Ar—COCH₂), 3.30 (Br, 4H, O—H, N—H), 3.54 (t, J=5 Hz, 2H, N—CH₂), 3.70 (s, 3H, O—CH₃), 4.03 (t, J=5 Hz, 2H, N—C—CH₂—O), 5.96 (s, 2H, Ar aromatic H), 6.60–6.84 (m, 3H, Ar'aromatic H); UV (H₂O) $\lambda_{max}$ 282 nm ($\epsilon=20,200$).

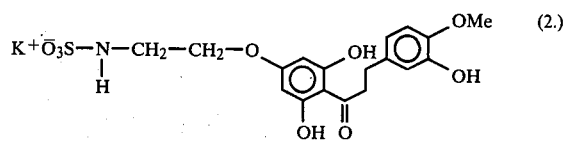

EXAMPLE V

The preparation of Example IV was repeated substituting 3-benzyloxy-4-methoxy-benzylamine

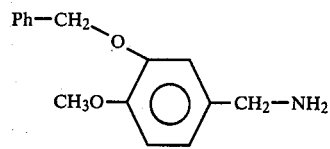

for the dihydrochalcone amine therein employed. This gives rise to the catechol sulfate addition product (mp 87°–8°) in 85% yield and the ultimate sulfamate salt in 81% isolated yield.

EXAMPLE VI

The preparation of Example IV was repeated substituting aniline

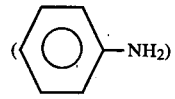

for the dihydrochalcone amine therein employed. A 40° temperature is employed during coupling and a 66% yield of the addition product was obtained. This product underwent hydrolysis to give the desired sulfamo compound.

EXAMPLE VII

In each of the foregoing examples, the sulfamates have been present as potassium salts. By varying the base employed from KOH to NaOH or Ca(OH)₂, other equivalent salts can be formed.

EXAMPLE VIII

To demonstrate the utility of the present invention, a sample of the dihydrochalcone sulfamate made using this invention in Example IV was dissolved in water at various concentrations. A trained taste panel tasted these samples and determined that the dihydrochalcone had a pleasant sucrose-like sweet taste and would be suitable for use as a synthetic sweetener. On average, it was found to be 352 times as sweet as sucrose on a weight basis.

What is claimed is:

1. The process for sulfamation of primary organic amine which comprises the steps of:
   (a) contacting said primary organic amine in liquid phase with catechol sulfate at a low to moderate temperature for a period of from about 1 hour to about 72 hours, thereby forming an O-2-hydroxyphenyl sulfamic acid ester, and
   (b) hydrolyzing the O-2-hydroxyphenyl sulfamic acid ester by contacting it with a strong base at a temperature of from 50° C. to 200° C. for from 1 minute to 12 hours, thereby forming the sulfamic acid salt corresponding to said strong base.

2. The process of claim 1 wherein in Step (a) the amount of said primary organic amine is at least two moles per mole of catechol sulfate.

3. The process of claim 1 wherein in Step (a) a tertiary amine is present and the amount of said primary organic amine plus tertiary amine is at least two moles per mole of catechol sulfate.

4. The process of claim 1 wherein in Step (a) said liquid phase comprises a liquid which dissolves the catechol sulfate and said amines.

5. The process of claim 4 wherein in Step (a) said low to moderate temperature is from $-30°$ C. to $50°$ C.

6. The process of claim 5 wherein in Step (b) the amount of strong base is an amount that provides one equivalent of base for each equivalent of acid groups on said amines plus about 1.0 to 1.5 equivalents of base per equivalent of O-2-hydroxyphenyl sulfamic acid ester.

7. The process of claim 6 wherein in Step (b) an aqueous reaction medium is employed.

8. The process of claim 7 wherein in Step (b) a temperature of 50° to 120° C. and a time of 0.5 to 4 hours is employed.

9. The process of claim 8 wherein in Step (a) the amount of said primary organic amine is about two moles per mole of catechol sulfate.

10. The process of claim 8 wherein in Step (a) a tertiary amine is present and the amount of said primary organic amine plus tertiary amine is about two moles per mole of catechol sulfate.

* * * * *